US005913315A

United States Patent [19]

Todd

[11] Patent Number: 5,913,315

[45] Date of Patent: Jun. 22, 1999

[54] HAIR TATTOO APPARATUS AND METHOD

[76] Inventor: Mark D. Todd, 1815 Lake Rd., Webster, N.Y. 14580

[21] Appl. No.: 09/059,874

[22] Filed: Apr. 14, 1998

Related U.S. Application Data

[63] Continuation-in-part of application No. 08/901,815, Jul. 28, 1997, Pat. No. 5,848,599, and a continuation-in-part of application No. 08/926,347, Sep. 9, 1997, Pat. No. 5,823, 204, and a continuation-in-part of application No. 09/005, 734, Jan. 12, 1998.

[51] Int. Cl.[6] .......... A61K 7/13

[52] U.S. Cl. .......... 132/208; 132/206; 132/211

[58] Field of Search .......... 132/206, 207, 132/208, 221, 223, 224, 225, 319; 606/116

[56] References Cited

U.S. PATENT DOCUMENTS

| | | | |
|---|---|---|---|
| D. 315,968 | 4/1991 | Rizzuto et al. . | |
| 1,591,207 | 7/1926 | Berthelsen | 132/225 |
| 1,696,823 | 12/1928 | Walsh | 132/225 |
| 1,709,981 | 4/1929 | Headington . | |
| 2,274,170 | 2/1942 | Stanley . | |
| 2,705,499 | 4/1955 | Breeeze . | |
| 3,433,232 | 3/1969 | Garrett . | |
| 3,898,357 | 8/1975 | Miller et al. . | |
| 4,169,169 | 9/1979 | Kitabatake . | |
| 4,261,375 | 4/1981 | Anderson | 132/224 |
| 4,522,836 | 6/1985 | Humason et al. . | |
| 4,594,276 | 6/1986 | Relyea . | |
| 4,739,151 | 4/1988 | Smal | 132/225 |
| 5,421,765 | 6/1995 | Lehmann et al. . | |
| 5,470,351 | 11/1995 | Ross et al. . | |

FOREIGN PATENT DOCUMENTS

| | | |
|---|---|---|
| 341869 | 2/1931 | United Kingdom . |

*Primary Examiner*—Gene Mancene
*Assistant Examiner*—Pedro Philogene
*Attorney, Agent, or Firm*—Jaeckle Fleischmann & Mugel, LLP

[57] ABSTRACT

In accordance with this invention, there is provided an image transfer sheet to transfer a colored image to hair. The image transfer sheet comprises at least a first gel layer, a color layer, and a second gel layer. The present invention includes a process to use the image transfer sheet. The process entails contacting the sheet to hair and applying sufficient heat and/or pressure to the sheet and hair so the colored image transfers to the hair.

32 Claims, 6 Drawing Sheets

HAIR TATTOO APPARATUS AND METHOD

CROSS-REFERENCE TO RELATED PATENT APPLICATION

This application is a continuation-in-part of applicant's patent applications U.S. Ser. No. 08/901,815, filed on Jul. 28, 1997, Pat. No. 5,848,599, Ser. No. 08/926,347, filed Sept. 9, 1997, Pat. No. 5,823,204 and 09/005,734 filed Jan. 12, 1998, pending, all of which are incorporated by reference.

FIELD OF THE INVENTION

The invention relates to image transfers, and, in particular, to a transferable image comprising a colored image wherein the image transfers to hair and an apparatus and a process to do the same.

BACKGROUND OF THE INVENTION

Des. Pat. No. 315,968 discloses a hair crimping appliance comprising a male portion and a female portion. The male portion of the device depicted comprises a protruding heart-shaped die. The female portion of the device comprises a heart-shaped recess which extends through the entire thickness of the female die plate. However, that device does not produce a durable image or a sharply-defined colored image in hair and does not transfer an image to hair.

An object of this invention is to provide a device and an image sheet that produces a durable, colored, sharply defined, crimped hair image.

Another object of this invention is to provide a process to transfer a colored image from an image sheet to hair.

Another object of the present invention is to provide an image sheet that transfers a colored image to hair.

SUMMARY OF THE INVENTION

In accordance with this invention, there is provided an image transfer sheet to transfer a durable or colored image or both a durable and colored image to hair. The image transfer sheet comprises an image release substrate and one or more superior to layers. In one embodiment the substrate has one superior layer that comprises a gel for holding a crimped image in the hair. The gel may be clear or colored, including one or more colors. The image may be two or three dimensional, depending upon the apparatus used to apply the image to the hair. The invention also contemplates an image wafer comprising one or more layers separate from the transfer sheet.

The two layer embodiment has a transfer substrate, a first gel layer and a color layer. The gel may be clear or colored. The color layer comprises one or more colors. The color layer also comprises a gel. The first layer may be water soluble or may comprise one or more permanent or semi-permanent materials. For example, the pigment used for color in the second layer may be of water durable or water repellent material. If the hair becomes wet, the water durable or water repellent material will protect the underlying first layer and extend the life of the image in the user's hair. The three layer embodiment comprises a first gel layer, a second or color layer, and a third, gel layer. The third layer protects the color layer and provides added thickness for handling.

The superior layers may include one or more auxiliary materials for both aesthetic and practical purposes. These materials include glitter for ornamentation and magnetic, ferromagnetic, or electrostatic particles to help hold the transfer sheet or image in the image transfer apparatus.

The present invention includes a process for transferring an image to a user's hair. The process includes steps for contacting the transfer sheet of the image wafer to hair and applying sufficient heat and/or pressure to the transfer sheet or image wafer and the hair to transfer the image to the hair.

The invention contemplates an apparatus, a method, transfer sheets and image wafers for two and three dimensional images. A further embodiment of the invention comprises a kit for applying a wet image to hair.

BRIEF DESCRIPTION OF THE DRAWINGS

The invention is illustrated by reference to the specification and the following drawings, in which like numerals refer to like elements, and in which.

DESCRIPTION OF THE PREFERRED EMBODIMENTS

Figure 1:
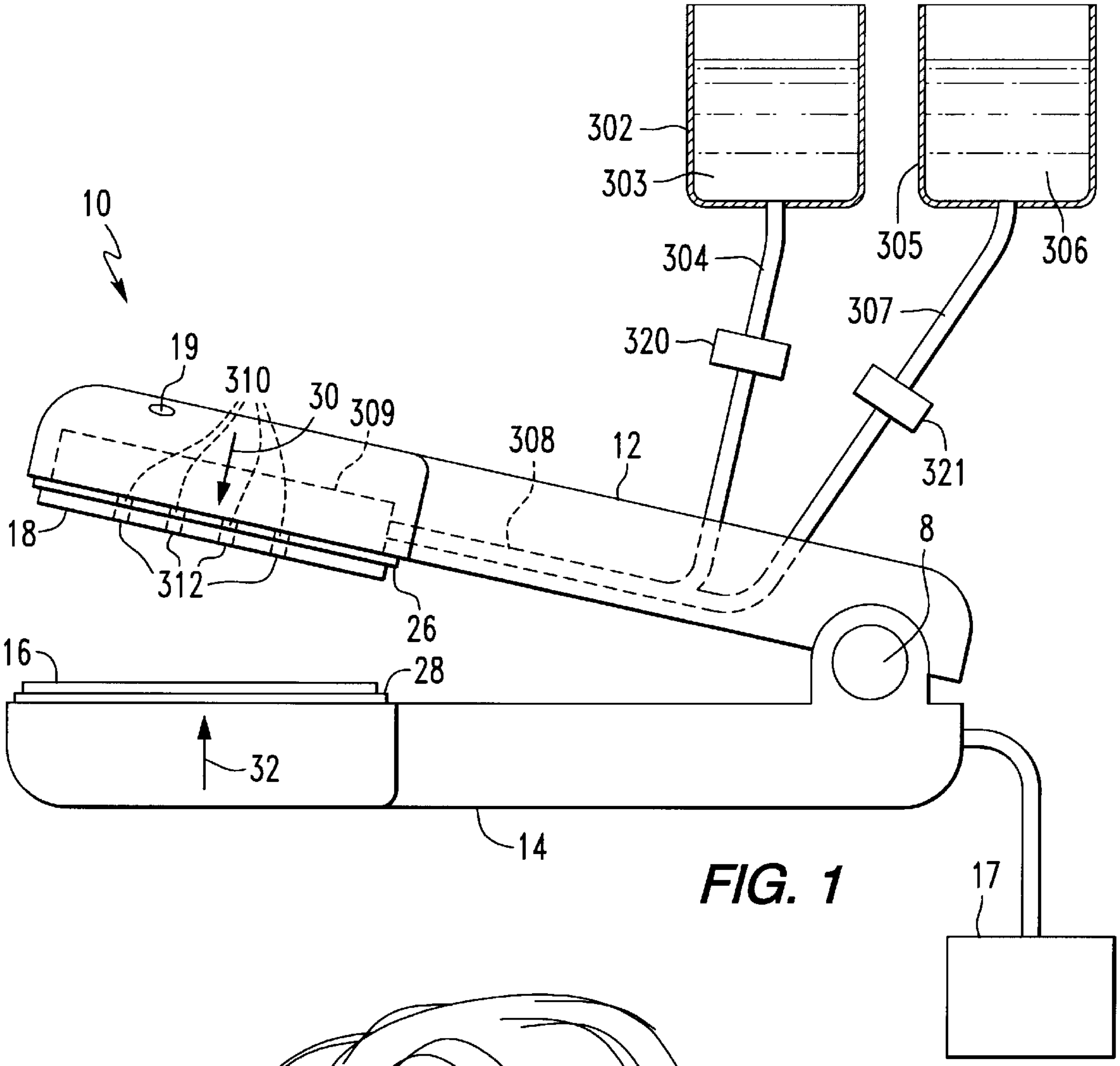
FIG. 1 is a perspective view of one preferred crimping iron for this invention.

FIG. 1 is a perspective view of one preferred device 10 of this invention. The device 10 comprises a top jaw 12, a bottom jaw 14, removable male and female dies 16, 18, an orifice 19, first and second backing plates 28, 26, and an electrical source 17. A hinge or pivot 8 attaches jaw 12 to jaw 14. Hinged jaws 12, 14 move in the respective direction of arrows 30, 32. The other reservoir holds color material. Since jaws 12, 14 are hinged the direction of arrows 30, 32, they are not necessarily linear and parallel with each other when jaws 12, 14 are moved.

Reservoirs 302,305 are optional. One holds a color fluid 303 and the other a release fluid 306 such as water, water vapor or steam that assists in releasing the hair tattoos as explained hereinafter. Vapor and steam generators (not shown) are well known appliances. Such appliances can be directly coupled to the conduit 307 if so desired. The fluids 303, 306 pass through conduits 304, 307 to manifold 308. Flow control valves 320, 321 regulate the flow of fluid to the manifold 308. The head 309 of manifold 308 has a number of orifices 310. Orifices 312 on the plate 18 are aligned with orifices 310 in the plate 18. Color and/or release fluids are discharged from the orifices 312.

The first backing plate 28 connects to one of the jaws 12, 14 (in FIG. 1: jaw 14) and the second backing plate 26 connects to the other jaw. The female die 18 connects to the first backing plate 28 while the male die 16 connects to the second backing plate 26. The dies 16, 18 and backing plates 26, 28 comprise a conventional heat conductive material and connect to an electrical source 17 that heats them during the operation of the device 10. Any source of electric power is sufficient including normal household ac current, or direct current, e.g., a battery.

Figure 2:
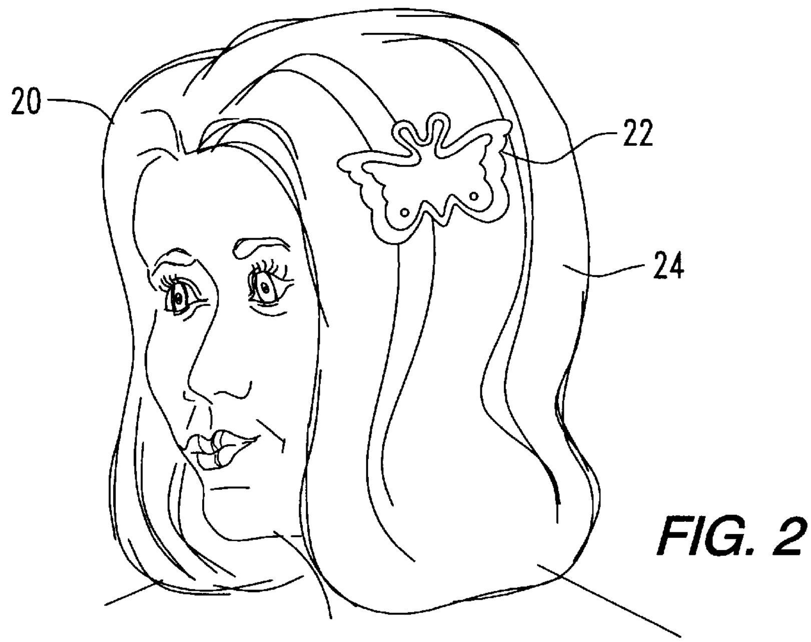
FIG. 2 is a perspective view of the crimped image produced by the crimping iron of FIG. 1.

The jaws 12, 14 close and the female die 16 engages the male die 18 and jaws 12, 14 transfer an image 22. In particular, device 10 transfers the image 22 onto hair 24. The image 22 as shown in FIG. 2 may be crimped and/or colored. The image 22 can be applied by a third party (not shown) or by a user 20. Such an image 22 can be any design including and not limited to lettering, alpha-numeric, inanimate objects or combinations thereof, i.e., FIG. 2 shows a butterfly design.

If the image 22 on the hair 24 is merely crimped, the image 22 is created with just the device 10 and dies 16, 18. The dies 16, 18 hold a design of the desired image 22, in this example a butterfly. A clear image transfer sheet or clear image wafer holds the image in place as described below.

Figure 3:
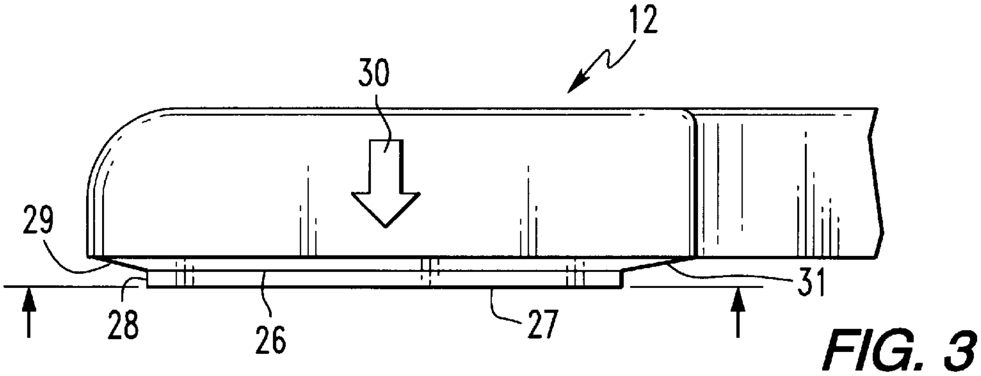
FIG. 3 is a partial side view of the top jaw of the crimping iron of FIG. 1.
Figure 4:
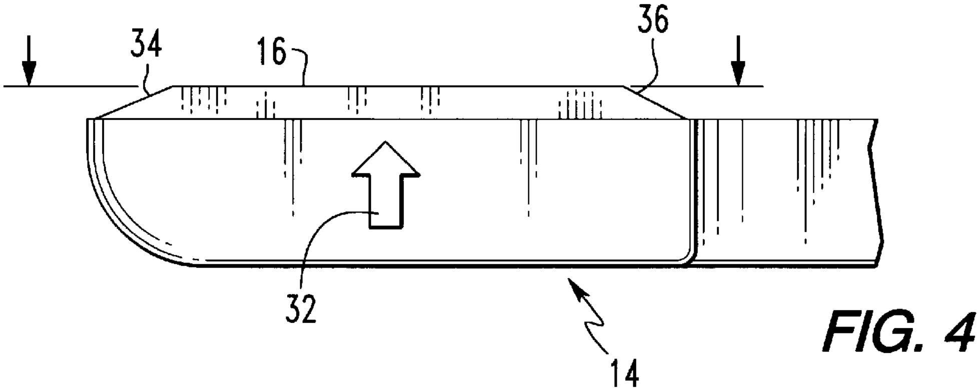
FIG. 4 is a partial side view of the bottom jaw of the crimping iron of FIG. 1.
Figure 5:
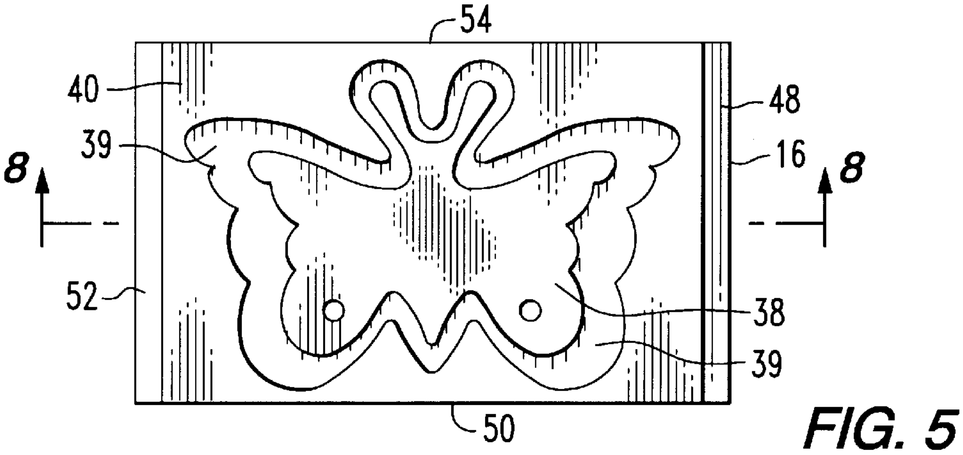
FIG. 5 is a top view of the female die plate of the crimping iron of FIG. 1.
Figure 6:
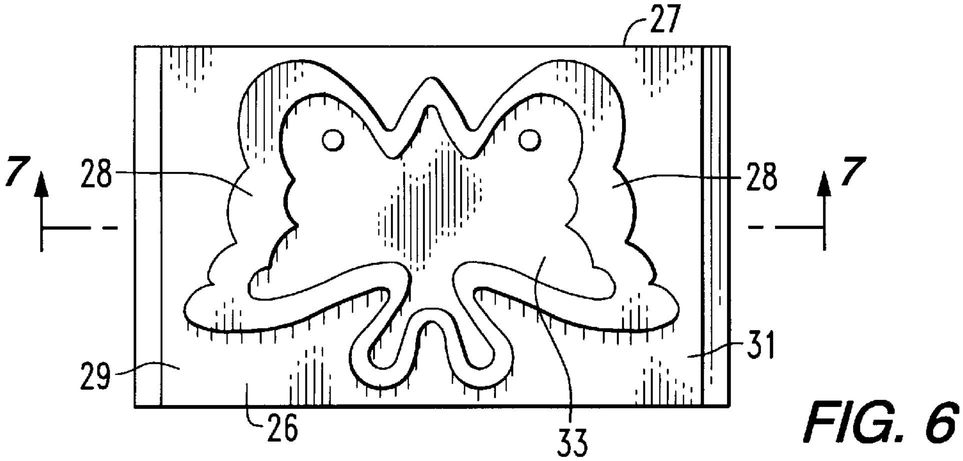
FIG. 6 is a top view of the male die plate of the crimping iron of FIG. 1.
Figure 12:
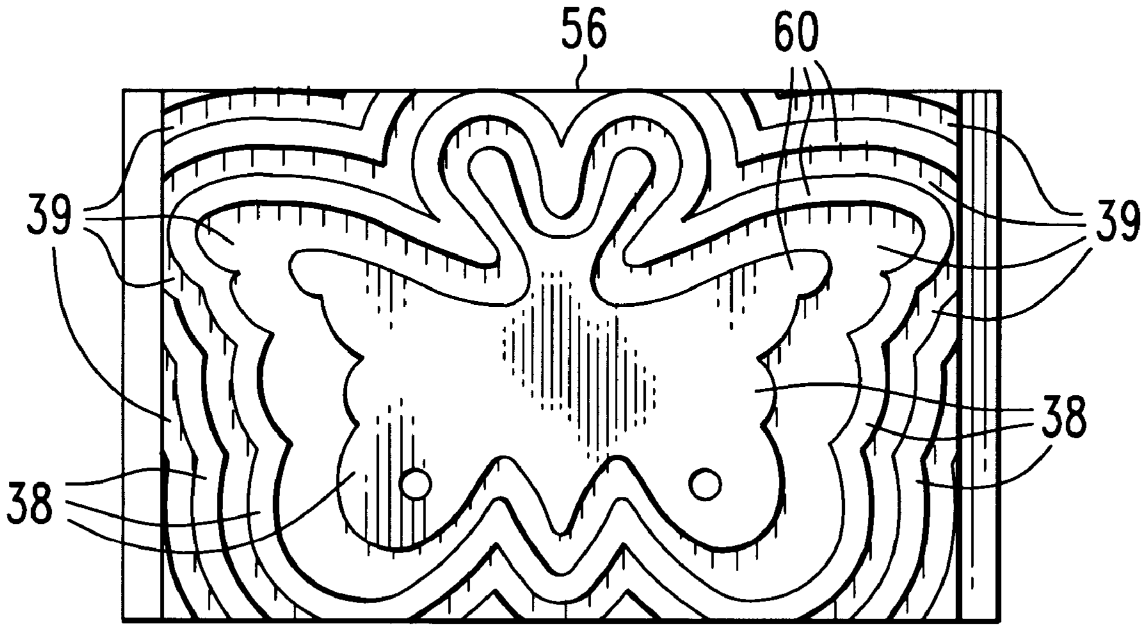
FIG. 12 is a top view of one female die plate of this invention.
Figure 13:
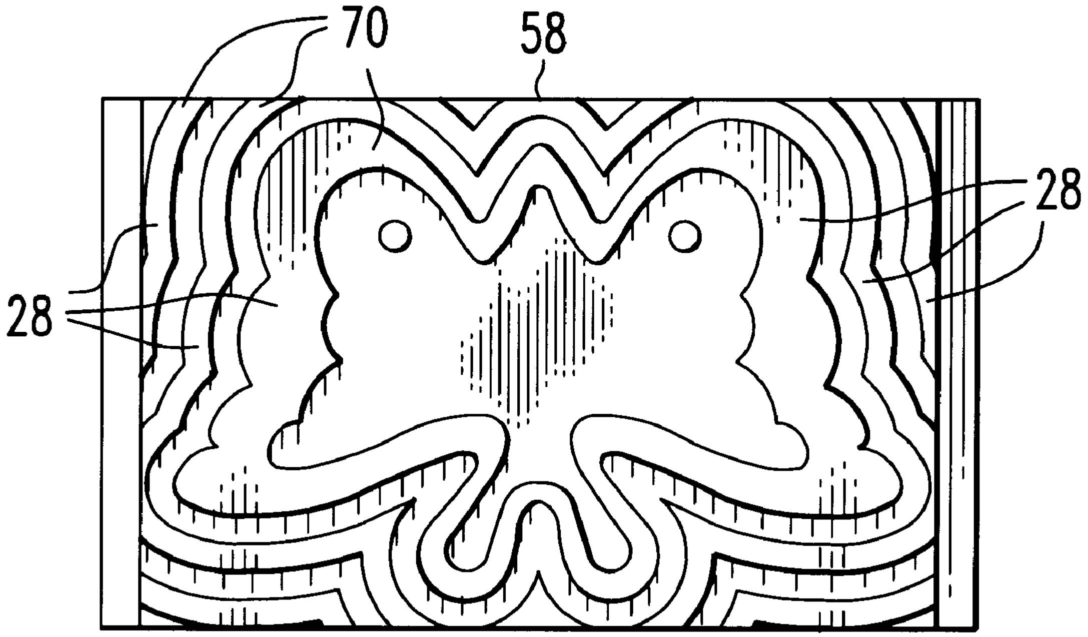
FIG. 13 is a top view of one male die plate of this invention.

FIG. 5 illustrates a top view of the die 18. Die 18 has a base 90 and a recess image 33 (channel) that receives the protruding extension 38. FIG. 6 illustrates a top view of the die 16. Die 16 has a base 37 and a protruding extension 38. Dies 16, 18 can comprise from zero to eight chamfered edges 48, 50, 52, 54, 29, 31, 93, and 91. The various alternate embodiments of the chamfered edges are illustrated in FIGS. 3 and 4. The protruding extension 38 and recess image 33 are each mutually chamfered as shown in FIGS. 12 (FIG. 5) and 13 (FIG. 6).

Figure 7:
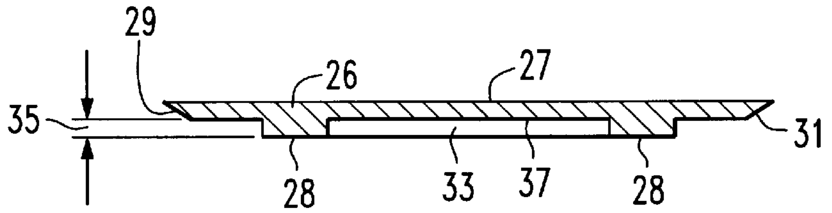
FIG. 7 is a cross-sectional view of FIG. 6 taken along the lines 7—7.

FIG. 7 is a cross-sectional view of FIG. 6 taken along the line 7—7. The protruding extension 38 has a height 35 of from about 0.016 to about 0.093 inches, extending from the top 94 of the base 37.

Figure 8:
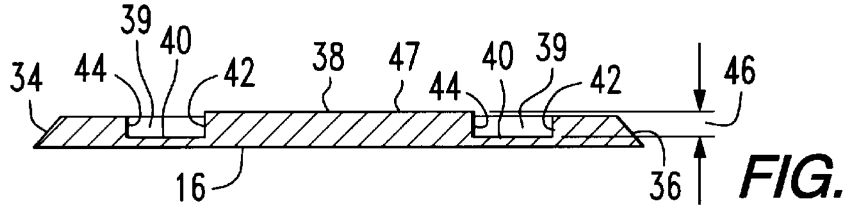
FIG. 8 is a cross-sectional view of FIG. 5 taken along the lines 8—8.

FIG. 8 is a cross-sectional view of FIG. 5 taken along the line 8—8. Within the base 90 is the recess image 33. Walls 40, 42, and 44 define the recess image 33. The distance 46 between the top 47 of base 90 and first backing plate 28 is from about at least about the thickness of one hair (a human hair is about 0.016 inches thick) to about 0.25 inches.

Figure 9:
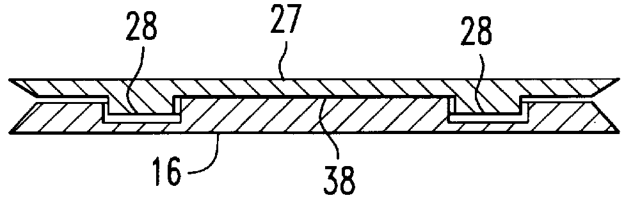
FIG. 9 is a schematic view illustrating how a user's hair is engaged when the male and female dies are engaged with each other.

FIG. 9 illustrates how the recess image 33 receives the protruding extension 38.

The process to transfer the image 22 onto hair 24 with the device 10 is as follows. The device 10 is heated to a sufficient temperature, i.e., over 110° F., to transfer the image 22 defined in the dies 16, 18. If desired, the hair is combed, held at the ends, and lightly sprayed with a hair setting spray to help keep the hairs aligned with each other. The hair 24 is placed between the jaws 12, 14. The jaws 12, 14 are held closed and the image 22 transfers to the hair.

The above transfer may be accomplished by other methods. One method is the device 10 attains a sufficient pressure to transfer the image 22, rather than heat. Another method transfers the image with a combination of sufficient pressure and temperature.

The device 10 illustrated in FIG. 1 is merely an illustration. The device 10 can be any device used on hair as illustrated in U.S. Pat. Nos. 4,870,250, 4,917,078, 5,025,850, U.S. Des. Pat. No. 316,762, U.S. Des. Pat. No. 315,968, U.S. Des. 315,967, and Des. Pat. No. 309,354. The disclosure of each reference is hereby incorporated by reference.

As mentioned above, the image 22 can also be colored and crimped. To color and crimp the image 22 on hair 24, a coloring agent is added to the process. The coloring agent can be added by various means. One embodiment provides an image on a transfer sheet that transfers the image to the hair. In another embodiment, hair dye is injected through an orifice 19 that receives a coloring agent, i.e., hair dye and/or hair gel (not shown), and directs such coloring agent to contact the channels within the dies 16, 18 and to hair 24. When the coloring agent contacts the hair 24, the coloring agent colors the hair 24.

Figure 10A:
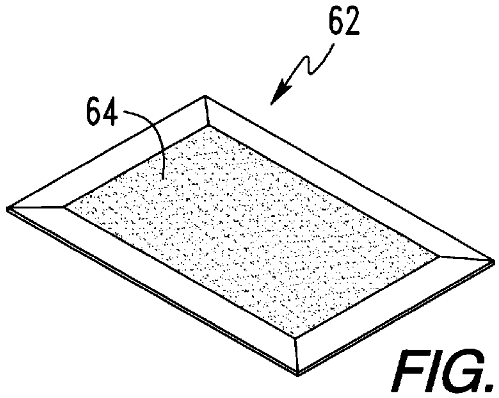
FIGS. 10(*a*) and 10(*b*) are top views of two different thermal transfer fabrics used in the device of FIG. 1.
Figure 10B:
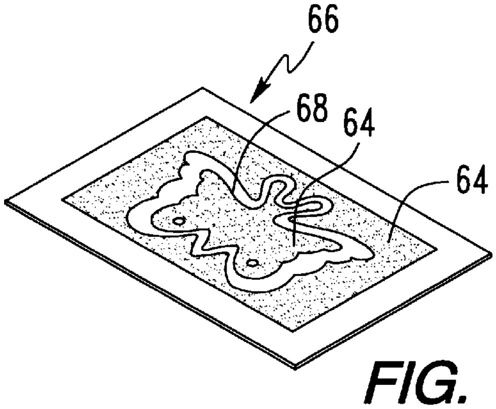

FIG. 10(*a*) illustrates substrate 62 comprising a transferable image 22 comprising one or more layers of hair gel and coloring pigment. One may use any of the hair coloring chemicals or compositions known to those skilled in the art. Thus, by the way of illustration and not limitation, one may use one or more of the hair colorings disclosed in U.S. Pat. Nos. 5,365,438, 5,273,739, 5,196,029 4,834,767, 4,775,527, 4,211,247, and the like. The disclosure of each of these United States patents is hereby incorporated by reference into this specification.

Another hair color material may be "GLITTER GEL." This gel is a washable, water-based hair color sold by Jerome Russell Cosmetics of Chatsworth, Calif. This material contains deionized water, sorbitol, propylene glycol, carbomer 940, triethanolamine, potassium sorbate, edta, quaternium-15, benzophenone-4, and fragrance. Still another hair color material 64 may be one or more of the "STAR GAZER" "semi permanent conditioning hair colors" sold by Star Gazer Products of London, England. Other suitable commercially available hair colors will be readily apparent to those skilled in the art.

Other hair color material includes food dyes mixed with citric acid or malic acid. One may also use basic dyes and salt, or textile dyes diluted with salts, detergents, and malic, citric, or tartaric acid. See, e.g., pages 336–351 of Volume 4 of the McGraw-Hill Encyclopedia of Science and Technology (New York, N.Y., 1977).

Another hair color material 64 is a washable material comprised of glitter. Glitter-containing coloring agents are commercially available; see, e.g., U.S. Pat. Nos. 4,915,935 (reflective particles in foam matrix), 3,675,005, and the like. The entire disclosure of each of these United States patents is hereby incorporated by reference into this specification.

By way of illustration, "scented body glitter" sold by Townley Distributors is also an acceptable hair color material. This material contains water, polyester glitter, propylene glycol, carbomer 940, triethanolamine, methylparaben, propylparaben, edta, and benzophenone-2.

One may use the "body cream gel" sold by Zaunder Brothers, Inc. of Freeport, N.Y. as a hair color material. This material contains purified water, propylene glycol, coated aluminum polyester film, carbomer-940, methylparaben, diavolidinyl urea, and propylparaben.

The preferred coloring agent is a water-soluble coloring agent. Such hair coloring agents are disclosed in U.S. Pat. Nos. 5,597,386 (water soluble coloring matter), 5,454,841 (water-soluble melanin), 5,281,240 (water soluble acid dyes), 4,981,485, 3,986,825, 3,973,901, 3,619,101 (water-soluble colored polymers), and the like. The entire disclosure of each of these United States patents is hereby incorporated by reference into this specification.

Substrate 62 may be any suitable material from which image 22 is transferable by either pressure and or heat. It is important that the substrate material be able to withstand heat and/or pressure sufficient to release the image from the substrate without melting the substrate or otherwise interfering with the image transfer process. It is also important that the substrate be sufficiently dense so that it can release the superior layers containing the image. By way of illustration and not limitation, substrate 62 may be made from fabric, parchment paper, other heat-resistant paper, etc. Such substrates comprise polytetrafluoroethylene ("PTFE"), fluoroethylene polymer, polyfluoro acrylate and mixtures thereof. Such polytetrafluoroethylene films or fabrics (fabrics also comprise filaments, threads or yarns) include those disclosed in U.S. Pat. Nos. 5,577,741, 5,622,565, 5,591,526 (PTFE fiber and fabric), 5,580,618, 5,578,131, 5,571,605 (PFTE fiber woven fabric), 5,556,708, 5,549,966 (composite, commingled fiber of fiberglass and PFTE) , 5,546,889, 5,510,176, 5,504,37, 5,502,389, 5,496,628 (a PTFE coated fiberglass substrate), 5,494,301, 5,489,370, 5,480,455, 5,478,372 (fiberglass fabric with a layer of PTFE membrane laminated to the fabric surface), 5,476,589, 5,468,923, 5,468,531, 5,468,529, 5,466,531, 5,456,983 (fiber of PTFE and fiberglass), 5,418,054, 5,417,499 (a liner containing PTFE and polyester fiber), 5,405,509, 5,399,418 (multiply textile fabric), 5,393,929, 5,387,300 (PTFE yarn), 5,358,678, 5,234,739, 5,217,666, 5,143,783, 5,037,457, 4,985,296, 4,650,833, 4,526,830 (coated woven or nonwoven fiberglass fabric), 4,347,278, 4,212,923, 4,025,639, 4,015,038 (fiberglass fabric coated with PTFE), 3,560,327, 3,486,961, and the like. The entire disclosure of each of these United States patents is hereby incorporated by reference into this specification. In particular, a preferred polytetrafluoroethylene fabric material is commercially available "TEFLON® BAKEWARE LINERS" from E.I. DuPont deNemours and Company of Wilmington, Del. This material is a fluoropolymer/fiberglass based laminate which is prepared by coating a fiberglass substrate with fluoropolymer.

The entire top surface of substrate 62 consists of one or more superior layers including an image 22 of two or three dimensions and optionally having one or more colored portions.

In the embodiment illustrated in FIG. 10(*b*), an outline of a butterfly 68 has been impressed within substrate 66, and image 22 is disposed on selected areas of the substrate 66. The use of this will selectively transfer coloring agent to portions of the hair being treated.

It will be apparent to those skilled in the art that many different coloring agents, and/or many different combinations of coloring agents, may be disposed on all or selected portions of the films or fabrics 62 or 66.

Figure 11:
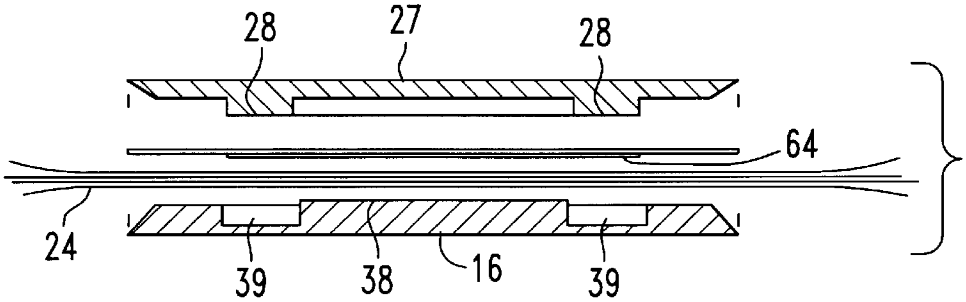
FIG. 11 is a schematic representation illustrating the interaction of the male die plate, the female die plate, the thermal transfer material, and the hair to be treated.

FIG. 11 is a schematic representation of the use of applicant's device. The hair 24 to be treated is compressed within dies 16 and 18, and contacts image 22. The resulting treated hair will not only be selectively colored, but it also will be shaped by the dies.

Figure 14:
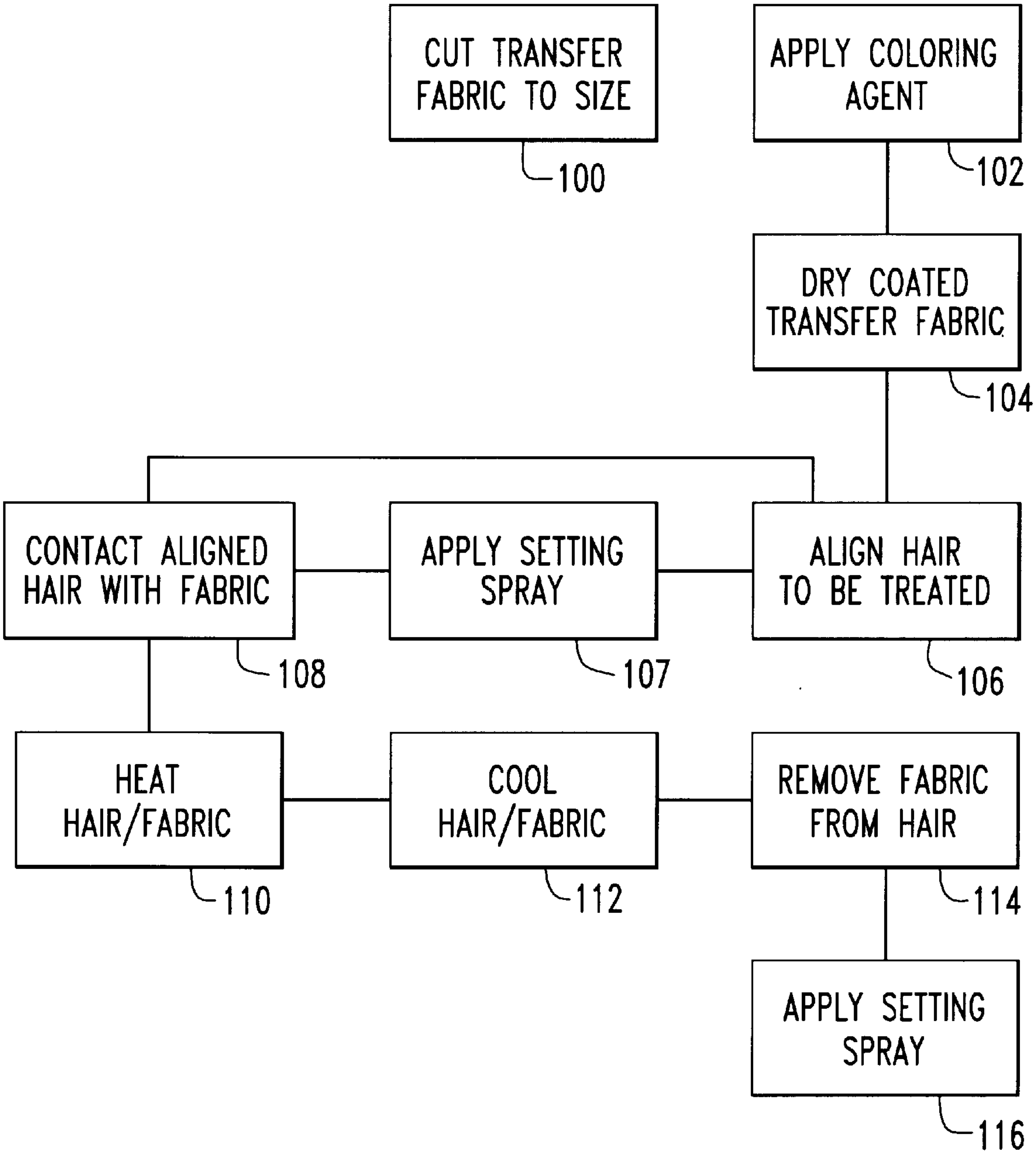
FIG. 14 is a flow diagram illustrating one preferred process of this invention.
Figure 15A:
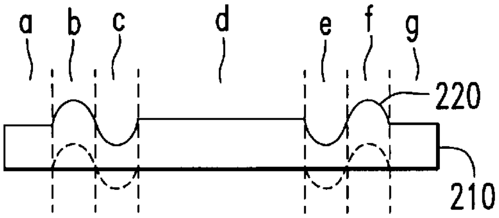
FIGS. 15 (*a*)–15 (*g*) illustrate a process to fabricate image transfer sheets and image wafers.
Figure 15B:
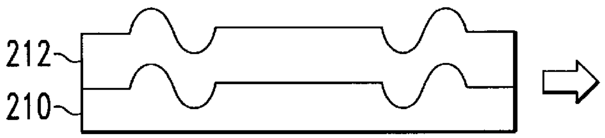
Figure 15C:
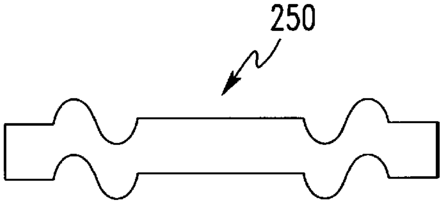
Figure 15D:
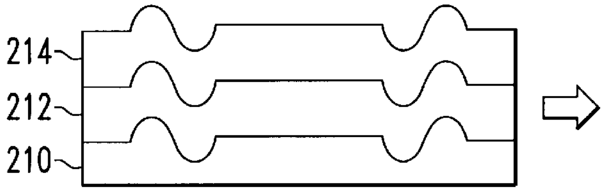
Figure 15E:
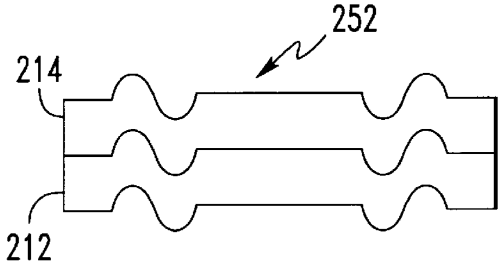
Figure 15F:
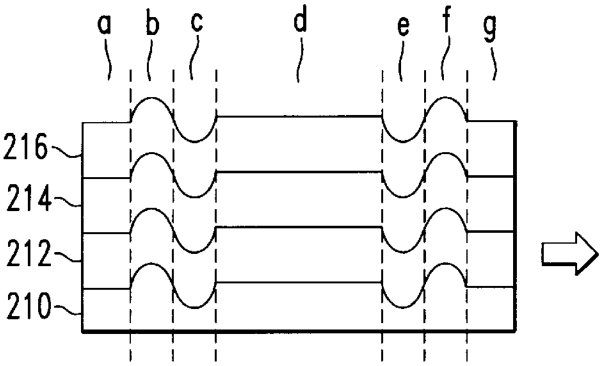
Figure 15G:
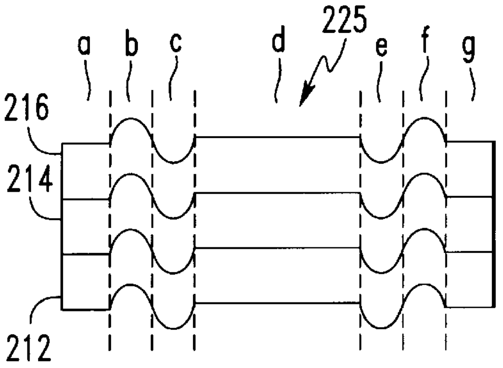

FIG. 14 is a flow diagram illustrating one preferred process of the invention. The transfer material is cut to substrate size as shown in step 100. The substrate 62 generally should be cut into a desired shape with a surface area no larger than about 18 square inches and, preferably no larger than about 10 square inches. Preferably, the substrate 62 is cut into a substantially rectangular or square shape. In another embodiment, not shown, the substrate 62 is cut into a larger portion that covers a substantial part of the back of a prospective user's head.

In one embodiment, at least one (and preferably at least about 4) hole is punched into the cut transfer substrate 62 so the substrate may be properly aligned onto said plate by means of double sided tape. Alternatively, guide lines are imprinted upon the dies.

The image 22 in step 102 is applied to the substrate 62. The application is by conventional means such as painting, silkscreening, printing, etc. Preferably, each color in the image 22 is separately applied to the substrate 62.

Thereafter, in step 104, the coated transfer substrate 62 is dried by conventional means such as hot air, infrared radiation, microwave radiation, etc. Alternatively, or additionally, the transfer substrate may be sprayed with setting spray.

In step 106, the hair to be treated is aligned so that the individual hairs are substantially parallel to each other. This may be done by conventional means, such as brushing or combing such hair.

In step 107, which is optional, after the substrate 62 has been cut to the desired size, setting spray is applied to the hair to be treated. Alternatively, one may omit the setting spray step and go to step 108.

If a setting spray is used in step 107, it is preferred that a thermal active setting be used. In one embodiment, the setting spray described in U.S. Pat. No. 4,007,005 is used.

In step 108 the hair contacts the surface of the fluoropolymer-containing substrate that is clear or colored gel. Such contact may be effected by the means disclosed in FIG. 11. Alternatively, one may wrap the aligned hair and the substrate on a curling iron, waffle iron, and the like.

Thereafter, generally within a matter of seconds, the hair/substrate composite structure is preferably heated to a temperature of at least about 110 degrees Fahrenheit and, more preferably, at least about 180 degrees Fahrenheit in step 110. In one embodiment, the hair/substrate composite is briefly subjected to a temperature in excess of 300 degrees Fahrenheit. In another embodiment, the hair/substrate composite is subjected to pressure at ambient temperature.

It is preferred to subject the hair/substrate composite to the desired temperature for at least about 20 seconds. In one embodiment, the hair/substrate composite is heated for about 30 to about 150 seconds.

Thereafter, in step 112, the treated hair/substrate composite cools to ambient temperature, generally over a period of from about 2 to 5 minutes. Thereafter, the substrate material is removed from the hair in step 114. Finally, hair spray or setting spray may optionally be applied in step 116.

The following examples are presented to illustrate the claimed invention but are not to be deemed limited thereof. Unless otherwise specified, all temperatures are in degrees Fahrenheit.

EXAMPLE 1

In the experiment of this example, a crimping iron sold under the name of "BELSON GOLD'N HOT" by Belson Products of Miami Lakes, Fla. was modified by replacing the crimping plates with the male and female dies illustrated in FIGS. 5 and 6.

A transfer substrate 62 was prepared from commercially available bakeware liners (TEFLON®). These substrate bakeware liners comprise a fiberglass substrate bonded to exterior layers of polytetrafluoroethylene. The TEFLON® substrate was cut into rectangular shapes which were 4.5"× 2.0".

The cut substrate sheets were then embossed with the male and female dies on the crimper to produce the butterfly pattern depicted in FIGS. 5 and 6. Colored gel is applied to the indented portions of the substrate (see, e.g., sections 39 and 28 FIGS. 5 and 6, respectively).

Onto 39 of the butterfly image (see FIG. 5) was painted a gold "GLITTER GEL" washable hair color that is sold by Jerome Russell Cosmetics of Chatsworth, Calif. Onto section 38 of 5 the butterfly image (see FIG. 5) was painted a purple "GLITTER GEL" which also was obtained from the Jerome Russell Cosmetics Company.

The painted butterfly images were allowed to air dry 36 hours. Next, a substrate square containing one of these images was placed between the jaws of the Belson crimping iron. The male die plate was above the colored section of the substrate and the colored section of the substrate was substantially congruent with the corresponding sections on the female die plate.

A young woman, about 26 years old, was used in this experiment; she had medium blonde hair. Her hair was washed with shampoo, rinsed and dried to remove substantially all foreign matter from it. Thereafter, a section of her hair, roughly about 5 inches by about 1 inch, was combed at about a 35 degree angle while being held between a hairdresser's fingers.

The crimping iron was heated so that its jaws were at a temperature of about 180 degrees Fahrenheit. Thereafter, the combined hair was disposed between the jaws of the preheated crimping iron, and the jaws were closed in order to compress the hair and the substrate together. The jaws were closed for about 40 seconds.

Thereafter the jaws of the crimping iron were opened and pulled away from the subject's head; and the hair was gently allowed to drop to her head.

The hair was allowed to cool for two minutes. Thereafter, the substrate was removed from the hair.

The hair had an indented portion that was colored with gold and green glitter; the areas between the gold and green glitter were sharply demarcated.

EXAMPLE 2

The experiment of Example 1 was repeated, with the exception that the jaws were reversed. A raised, colored portion of hair was produced instead of an indented portion.

EXAMPLE 3

The procedure of Example 1 was followed, with the exception that the central "body" area of the butterfly was colored with blue "STAR GAZER" conditioning hair color (obtained from Stargazer Products of London, England).

EXAMPLE 4

The procedure of Example 1 was followed with the exception that the modified BELSON crimping iron was returned to its original state with its original flat plates, and with further exception that the image to be transferred was painted upon a non-embossed substrate sample. Although an indented image was not obtained, a clearly defined, colored image 22 was in fact transferred.

EXAMPLE 5

The procedure of Example 4 was followed with the exception that an image in the shape of a horse was transferred.

EXAMPLE 6

The procedure of Example 1 was followed with the exception that an image of a "peace sign" was transferred. In the experiment of this example, red and blue "CRAYOLA" washable finger paints (sold by Binney & Smith, Inc. of Easton, Pa.) were used.

EXAMPLE 7

The procedure of Example 1 was substantially followed, with the exception that Zotos interchangeable flat and crimping iron (sold as model Z600 by Zotos International Corporation of Darien, Conn.) was used.

EXAMPLE 8

The procedure of Example 1 was substantially followed, with the exception that a Babyliss "pro convertible crimper and straightener in one" iron was used. This iron was obtained from the Babyliss Company of Belgium.

EXAMPLE 9

The procedure of Example 1 was substantially followed, with the exception that strips of colored substrate were disposed on the surface of a model 1182 curling iron sold by "Hot Tools, Inc. of El Paso, Tex. In the experiment of this example, rectangular strips of colored substrate were applied to the hair so that the coloring material contacted the hair, and the curling iron was then wound around the hair to be colored.

EXAMPLE 10

The procedure of Example 9 was substantially followed, with the exception that a model 1110 curling iron from Hot Tools, Inc. was used, and the strips of colored substrate were in an elongated zig-zag shape.

EXAMPLE 11

The procedure of Example 9 was substantially followed, with the exception that a model 1181 curling iron from Hot Tools, Inc. was used. In this example, the strips contained multi-colored designs.

Other aspects of the invention include processes for making a hair tattoo image transfer sheet and a hair tattoo wafer. These further aspects of the invention are best understood with reference to FIGS. 15(*a*)–15(*e*)

The process to fabricate the image transfer sheet 225 begins by providing a substrate 210 of image releasable material. This material is compatible with superior layers that will be subsequently deposited thereon. "Compatible" means that the subsequent layers may be readily released from the substrate 210. In the preferred embodiment of the invention, substrate 210 is made of a resin bonded fluoropolymer. The polymer is selected from the group consisting of polytetrafluoroethylene (PTFE), fluoroethylene polymer, polyfluoro acrylate and mixtures thereof. shown in 15(*a*), the substrate 210 has at least an upper surface with an image 220. The dotted lines show that the lower surface may also have the pattern. The image 220 is any suitable design such as a logo, emblem, symbol, or an image representative of flora, fauna, an inanimate object, a geometric pattern or other pattern, a sports logo, or representation of a real or imaginary person such as a comic strip character. The image 220 may also represent alphanumeric characters. Likewise, the image 220 may be any combination of the above such as an alphanumeric character included within an image. For example, the image 220 may be an image of a professional sports team with player's uniform number. A typical, suitable substrate material is the TEFLON® PTFE material described above in connection with the TEFLON® bakeware liners manufactured by E.I. DuPont.

In the next step, a first layer 212 of a first gel is deposited on the substrate 210 over the image 220. The layer 212 is conformably deposited on the upper surface of the substrate 210 so that the image 220 is repeated in the gel layer 212. Those skilled in the art will appreciate that the sketches shown in FIGS. 15(*a*)–15(*e*) are schematic representations. As such, the relative thickness of the different layers are exaggerated in order to demonstrate the features of the invention. The gel layer 212 may be printed onto substrate 210 by any suitable printing process, including painting and silk screen processes. In other words, the gel layer 212 is in effect painted on the surface of the substrate 210. Thus, gel layer 212 readily provides a conformal layer so that the pattern of the image 220 is repeated in the upper surface of the gel layer 212.

In the single layer embodiment, the first layer 212 may be a clear gel. The resulting image in the user's hair will be an embossed or engraved image without color. The transferred gel will help hold the image in place. The first gel layer may have one or more colored portions. The gel layer 212 generally comprises glycol, water and other suitable binders. Metallic, magnetic, and electrostatic particles may be added to the gel 212 or to other superior layers. The purpose of these particles will be explained later. The coloring material may include glitter color. The transfer sheet can be dried as described above and below. Once dried, the single layer image may be removed from the transfer sheet to provide a one layer image wafer 250 as shown in FIG. 15 (*c*).

In the two layer embodiment, the first layer 212 is a clear or single colored gel. As shown in FIG. 15(*d*), a second layer 214 is added over the first gel layer 212. This second layer 214 may be printed onto the substrate 210 by any suitable printing process, including a silk screen process. The second layer has a plurality of regions a–g. Likewise, each of the layers of the sheet 225 has a corresponding region a–g. The different regions of the sheet 225 may be colored with different colors in order to produce the desired effect. The transfer sheet can be used in the transfer apparatus as described above. As an alternative, the layers 212, 214 can be removed from the transfer sheet to provide a transfer wafer 252 as shown in FIG. 15(*e*).

Turning to FIG. 15(*f*), there is shown the final step in forming the three layer embodiment. A third layer 216 comprising a second gel is deposited or otherwise coated over the second layer 214. The third layer 216 is an optional layer. The third layer 216 serves to seal the second layer 214 and prevent damage to layer 214 and thus increase the life span of the hair tattoo. The material for the third layer 216 may be the same or different from the material used as the gel for the first layer 212.

Upon completion of the steps shown in FIG. 15 (*d*), the user has a transfer sheet apparatus. The transfer sheet may be then placed in the suitable die plate of the device 10 and the image transferred to the user's hair. After the image has been heated or subjected to pressure and transferred, the device 10 is removed leaving the transfer sheet on top of the person's hair. Then the substrate 210 is carefully removed from the image 22 leaving the tattoo image 22 in the person's hair. This leaves a two or three dimensional image in the user's hair. The number of dimensions depends upon the type of die plates used.

The image formed by layers 212, 214, and 216 should be substantially dry before it is applied to the user's hair. Under ambient conditions, it takes anywhere from 4 to 6 hours for the image to dry by itself. However, drying can be accelerated by subjecting the structures shown in FIG. 15 to microwave radiation, forced hot air, or ultraviolet radiation. The microwave radiation heats the structure and dries off the excess water within the gel layers and the color layer. It is also possible for the user to apply moist color material to the transfer sheet and crimp the hair with a wet transfer sheet in a heated transfer apparatus.

A three layer image wafer 230 of layers 212, 214, and 216 may be separated from the substrate 210 prior to the transfer operation. Once separated, the resulting image tattoo wafer 230 is shown in FIG. 15(*f*). This structure 230 is relatively delicate and should be carefully handled.

The image tattoo wafer 230 is placed in the device 10 for fixing the wafer 230 to a person's hair. The device 10 has plates 26,28 that are coated with a release material, such as PTFE. The plates have opposing surfaces that are both flat, one with a raised design and one with relief design corresponding to the image of the hair tattoo, or one with a flat surface and the other with a raised or relief design corresponding to the image of the hair tattoo. Other release materials are acceptable so long as they withstand the heat and pressure applied by the device 10 to fix the wafer 230 to hair.

The image can be fixed using pressure, abrasion, or friction and with or without heat. For a transfer sheet such as shown in FIG. 15(*d*) a platen plate, is placed on the inside surface of the hair between the hair and the user's head. The platen plate has either a flat surface or a surface with a design corresponding to the image. The transfer sheet is placed image down on the opposite, outside surface side of the hair. A suitable frictional transfer instrument, such as a stylus, roller or other frictional applicator, rubs, rolls or otherwise engages the outside surface of the release substrate 210. Application of friction and/or pressure and the attendant heat of rubbing releases the image from the substrate 210 and transfers the image to the hair. Transfer is further assisted by applying water, water vapor, or steam to the substrate while applying friction or pressure.

For example, the crimping apparatus of the invention has one or more fluid conduits 304, 307. At one end the conduits are coupled to a fluid reservoir 302, 305, such as water (hot and/or cold), water vapor or steam. The conduits carry the fluid to discharge orifices 312 located on the surfaces of the plates. As an alternative, water, water vapor or steam can be provided from an auxiliary apparatus, such a spray bottle or a vaporizer. A hair dryer can also apply auxiliary heat to release the tattoo from the substrate and fix the tattoo in the hair. Other release and fixing agents may be combined with water, vapor or steam or used in lieu thereof. The selection of the release and fixing agent depends upon the material of the substrate and the material of the hair tattoo.

Each of the superior layers 211, 214, 216 may include materials with optical characteristics for reflecting or transmitting light or blocking light. In still another embodiment of the invention, the layers may comprise ordinary watercolor paint such as finger paint distributed by CRAYOLA Crayon Company.

As indicated above, the layers may include metallic, magnetic, or electrostatic particles. Such particles hold either the transfer sheet 225 or the wafers 250, 252 and 230 in a desired position in the suitable die plate of the device 10. For example, a modified device 10 has either a permanent magnet or an electromagnet behind one of the die plates. The magnet behind the die plate attracts the ferromagnetic particles in the wafer 230. As such, the magnet holds the transfer sheet 225 and the image wafer 230 in place while the device 10 transfers the image to the hair. If the die plate is ferromagnetic metal, then the particles added to the layers 222, 214, and 216 may be magnetic particles. magnetic particles are attracted to the ferromagnetic die plate and hold the transfer sheet 225 and image wafer 230 in place during the transfer process. One may substitute electrostatic particles for magnetic particles in one or more of the layers 212, 214, and 216. Then one of the die plates is charged to a polarity opposite the electrostatic particles so that the transfer sheet 225 and image wafer 230 are held in place on the die plate.

The invention contemplates two and three dimensional images. Two dimensional images are formed by placing an image transfer sheet or an image wafer between two flat die plates and fixing the image to hair. As one alternate, the device 10 can have one flat plate and one plate with an embossed or engraved image that corresponds to the transferred image. In another embodiment, one of the die plates has a number of striations and resembles a comb. The other plate has a flat surface or embossed and/or engraved surface. Such a device is useful for relatively short hair. Another alternate is a kit where the user is supplied with materials for making image transfer sheets and image transfer wafers. The kit includes the substrates 210 described above and one or more gels with one or more colors. The kit contemplates the user preparing a two dimensional image in accordance with the above disclosure. However, the kit could also include embossed and/or engraved die plates.

All the above apparatuses and processes can be used on animals or on inanimate objects with hair-like features for example, dolls. The above process is particularly useful on hair that is relatively long and straight but also on wavy or curly hair.

Thus those skilled in the art will appreciate that the above image transfer techniques may also be implemented in connection with a curling apparatus as well as a crimping apparatus. The transferred image is an elongated design that wraps about the curling iron. The curling apparatus transfers the image to the outer surface of elongated curl. The invention includes such a modification.

Another embodiment of the invention is the application of skin tattoos to hair. There are numerous types of temporary skin tattoos such as the ones shown and described in U.S. Pat. Nos. 4,592,276, 4,169,169, and 4,522,864 which are incorporated by reference. Such tattoos may have a transparent or translucent backing that is designed to adhere to skin. I have discovered that such tattoos will also adhere to hair. Such temporary skin tattoos are released by contacting them to hair and applying heat, friction, moisture, steam, heat or combinations thereof. Such temporary tattoos can be applied to hair using one the apparatuses described above. The temporary tattoos are removed by using soap or detergent and water or by a mild oil, such as baby oil.

The hair tattoos of the invention are not limited to small portions of a person's hair. They can be made on a large, head-shaped substrate that cover substantial portions, including a majority, of the area of hair on a person's head. For example, the substrate is either shaped like a shower cap of a skull cap.

It is to be understood that the aforementioned description only illustrates embodiments of the invention. Changes can be made in the embodiments, ingredients and their proportions, in the sequence of combinations and process steps, and in other aspects of the invention without departing from the scope of the invention as defined in the following claims.

I claim:

1. An assembly for crimping and tattooing hair comprising:

first and second elongated arms coupled by a hinge at one of each arm; first and second plates located on the other ends of the arms, one plate opposite the other plate; one plate having an embossed surface including a design facing the other plate and the other plate having an engraved surface with a corresponding design facing the one plate;

a release coating on the surface of at least one of the plates;

a hair tattoo corresponding to the design of the plates and comprising a first material for separating from the release coating and for adhering to hair.

2. The apparatus of claim 1 wherein both plates have a release coating.

3. The apparatus of claim 1 wherein the release coating comprises a resin bonded fluoropolymer selected from the group consisting of polytetrafluoroethylene, fluoroethylene polymer, polyfluoro acrylate and mixtures thereof.

4. The apparatus of claim 1 wherein the plates and the hair tattoo are substantially flat.

5. The apparatus of claim 1 further comprising a plurality of discharge orifices in the plates and a conduit connectable at one end to a source of fluid and connected at the other end to the discharge orifices for carrying release fluid to the substrate to assist in releasing the hair tattoo from the substrate and in fixing the hair tattoo to the hair.

6. The apparatus of claim 5 wherein the fluid assists the release of the hair tattoo from the substrate.

7. The apparatus of claim 5 wherein the fluid assists the fixing of the hair tattoo to the hair.

8. The apparatus of claim 5 wherein the fluid is of the group consisting of water, water vapor, steam, and mixtures thereof.

9. An assembly for crimping and tattooing hair comprising:

first and second elongated arms coupled to a hinge at each one of their respective ends; first and second plates located on the other respective ends of the arms, one plate opposite the other plate, one plate having an embossed surface including a design facing the other plate and the other plate having an engraved surface with a corresponding design facing the one plate;

a hair tattoo transfer comprising a substrate with a release coating and a superior layer on the release coating of the substrate, said release coating for releasing the superior layer from the substrate upon the application of pressure and/or heat, said superior layer comprising a colored design corresponding to the design of the plates and comprising a first material for separating from the release coating and for adhering to hair.

10. The apparatus of claim 9 wherein the hair tattoo comprises a design with at least one color.

11. The apparatus of claim 10 wherein the release coating comprises a resin bonded fluoropolymer selected from the group consisting of polytetrafluoroethylene, fluoroethylene polymer, polyfluoro acrylate and mixtures thereof.

12. The apparatus of claim 9 wherein the surfaces of the plates and the hair tattoo are substantially flat.

13. A method for transferring a hair tattoo to hair comprising the steps of:

forming a hair tattoo with color and a design on one surface of a substrate with a release coating;

placing hair in contact with the hair tattoo; and releasing the hair tattoo from the substrate and transferring the hair tattoo to the hair.

14. The method of claim 13 wherein the hair tattoo is released by rubbing the other surface of the substrate to release the hair tattoo from the substrate and transfer the hair tattoo to the hair.

15. The method of claim 13 comprising the further step of applying heat to the hair tattoo to assist its transfer to the hair.

16. The method of claim 13 comprising the further step of placing a platen plate between the scalp of the person receiving the tattoo and the hair and rubbing the hair tattoo and the hair against the platen plate.

17. The method of claim 13 wherein the platen plate is flat.

18. The method of claim 16 wherein the platen plate has a design corresponding to the design of the hair tattoo.

19. The method of claim 15 further comprising the steps of applying to the substrate one of the group consisting of water, water vapor, steam, and mixtures thereof.

20. The method of claim 13 wherein the step of releasing the hair tattoo comprises one of the steps of the group consisting of rubbing, moisturizing, steaming, heating the hair tattoo and combinations thereof.

21. The method of claim 13 wherein the hair tattoo is shaped to conform to a substantial portion of a user's head.

22. The method of claim 21 wherein the hair tattoo covers more than half of the area of hair on a person's head.

23. A hair tattoo comprising a release substrate, a colored design on the substrate, said substrate and said design being large enough to cover a substantial portion of the area of hair of a person's head.

24. The hair tattoo of claim 23 wherein the substrate and the design cover the majority of the area of hair of a person's head.

25. A process for applying a hair tattoo with a removable, colored design to hair, comprising the steps of:

placing a hair tattoo with color and a design in contact with the hair; and applying sufficient heat or pressure or both to transfer and to fix the hair tattoo to the hair.

26. The method of claim 25 wherein the hair tattoo comprises a substrate with a release coating and a superior layer on the release coating of the substrate, said release coating releasing the superior layer from the substrate upon the application of pressure and/or heat.

27. The method of claim 25 wherein the release coating comprises a resin bonded fluoropolymer selected from the group consisting of polytetrafluoroethylene, fluoroethylene polymer, polyfluoro acrylate and mixtures thereof.

28. The method of claim 27 wherein the heat and/or pressure are applied by a pair of plates, one plate contacting the surface of the transfer sheet opposite the image and the other plate contacting the surface of the hair opposite the scalp.

29. The method of claim 25 wherein the hair tattoo comprises an image wafer with a first layer comprising at least one of the group consisting of gel and colored pigment and shaped in the form of a desired image.

30. The method of claim 29 wherein the plates comprise surfaces with raised and relief portions corresponding to the design of the hair tattoo.

31. The method of claim 29 wherein the surfaces of the plates are flat.

32. The method of claim 30 wherein one plate surface is flat and the other plate surface is in relief and corresponds to the design of the tattoo.

* * * * *